(12) United States Patent
Huh et al.

(10) Patent No.: US 8,232,453 B2
(45) Date of Patent: Jul. 31, 2012

(54) PROMOTER FROM SWEET POTATO RAN GTPASE GENE FOR THE HIGH LEVEL EXPRESSION IN PLANT-TISSUE CULTURE AND VECTOR USING THE SAME

(75) Inventors: Gyung Hye Huh, Gimhae-si (KR); Young Hwa Kim, Busan (KR); Bo Mi Kim, Uiseong-gun (KR)

(73) Assignee: INJE University Industry-Academic Cooperation Foundation, Gyeongnam (KR)

( * ) Notice: Subject to any disclaimer, the term of this patent is extended or adjusted under 35 U.S.C. 154(b) by 414 days.

(21) Appl. No.: 12/596,200

(22) PCT Filed: Aug. 12, 2008

(86) PCT No.: PCT/KR2008/004684
§ 371 (c)(1),
(2), (4) Date: Oct. 16, 2009

(87) PCT Pub. No.: WO2009/022845
PCT Pub. Date: Feb. 19, 2009

(65) Prior Publication Data
US 2010/0100986 A1    Apr. 22, 2010

(30) Foreign Application Priority Data
Aug. 13, 2007    (KR) .................. 10-2007-0081320

(51) Int. Cl.
*C12N 15/82* (2006.01)
*A01H 5/00* (2006.01)
*C07H 21/04* (2006.01)

(52) U.S. Cl. ........ 800/278; 800/288; 800/295; 800/298; 435/419; 435/468; 435/320.1; 536/24.1

(58) Field of Classification Search .................. None
See application file for complete search history.

(56) References Cited

U.S. PATENT DOCUMENTS

| | | |
|---|---|---|
| 2003/0126644 A1 | 7/2003 | Kim et al. |
| 2003/0186277 A1* | 10/2003 | Olek et al. ............... 435/6 |
| 2004/0023395 A1 | 2/2004 | Kim et al. |
| 2006/0253917 A1 | 11/2006 | Cooper |

OTHER PUBLICATIONS

Kwak et al. A strong constitutive gene expression system derived from ibAGP1 promoter and its transit peptide. (Plant Cell Reports (2007) vol. 26; pp. 1253-1262).*

Kwak, M.S. et al., "A strong constitutive gene expression system derived from *ibAGP1* promoter and its transit peptide," Plant Cell Rep, 26, 2007, pp. 1253-1262.

Kim, K.Y., et al., "A novel oxidation stress-inducible peroxidase promoter from sweetpotato: molecular cloning and characterization in transgenic tobacco plants and cultured cells," Plant Molecular Biology, 51: 2003, pp. 831-838.

* cited by examiner

*Primary Examiner* — Cathy Kingdon Worley
(74) *Attorney, Agent, or Firm* — Sughrue Mion, PLLC

(57) ABSTRACT

Disclosed herein are a promoter (SEQ ID NO.: 1) inducing high level expression of a target gene in plant tissue cultured cells, derived from the sweetpotato gene of Ran GTPase, small GTP binding protein, a plant transformation vector for carrying the same and a method for expressing a foreign gene in plant cell using the vector. The activity of promoter according to the present invention is higher than that of universal CaMV 35S promoter in transgenic suspension cultured cell lines, calluses and adventitious roots. Thus, the promoter is useful in the generation of transgenic cell lines including cultured roots to produce valuable materials such as medicinal or industrial proteins in a large quantities with plant tissue cultured cells.

15 Claims, 10 Drawing Sheets
(3 of 10 Drawing Sheet(s) Filed in Color)

[FIG. 1]

-1348
AACACATGGGGTTGGAGGAACAAAGTTAACTGATAGCCGTTACAATTATTACAACCGTCCG
CTTCACTTGAGAGCGTTTGGGTTGGGCTATGAACTACTAAAATATCTGTTCTAACTTATTCT
TGTATAAATAGTTTATGCCCTGCCTTGTAGGGCTATGAATTACTAAAATATCTGTTGAAC
TTATTCTTGTTTAAATAGTCTATTCGTCAATTTCTTAATCTCTCTCTCTCTCTCTCTCC
TAGTTGGTTGACAAAACTCCAAAAAAAAAAACAATTACTATTTAGCTTGCTCTAACAT
CATTGATAAAAGTTTATAGAGACTCTATATAATAATTTAAAGAGTTAATTCCATTTTTGTCT
TAGATTTATAGGTGACAATTCAGTTTTTAGTCAATTTTTATTAAAACATCCTCATTTGGTCCTA
GTATTACTGCGGCATGACTATTTTAGTCCTTCATCCTCATCGTTAAATACAAATGCATTTCA
GTCTTCTTATACAAAGTATGTTGAACCGTTATATTTTATTTTTTGAAAACATCC
ATAATTGAAGGGCCGAAACATCATTGAATTTAACGATATTTAACTGTTTGTAATTAATGA
CAAAAAATGGTTATGTTACAATAAAGTTTACAATACTAGGACCAAAAGTGAATGTCTAATAAAAGGAC
TTATGGACTGCCACCTATAAAGTTCATTGGAGTACTACTGGAGAAGTCATCCTAAGAAAATGAAGTT
CTCAAAGAGTATAAAGTTCATTCATTCGTCGTATGATGATGAATCTAAATTGAATCCCTTGTGCGTGCATA
CCCAAATGTAATTTTTTTTCAAGGATGATGATTAGGATTAATCCCAAAAAGTCAAAAACTAAAATCACCCAAATG
ATGAAGAGAATATGTTAATGGATTAGGATTAATCCCAAAAAGTCAAAAACTAAAATCACCCAAATG
AAGACTAGAATATGTTGAGTTTAGGATTAATCCCAAAAAGTCAAAAACTAAAATCACCCAAATG
GACCAAGTCTTGTGAGTTTAGGATTAATCCCAAAAAGTCCACAAATAGCCACAAATAAAATATCCACA
TAAAAAACAAAAAGAAGTCTATAAAGTCCACAAATAGCCACAAATAAAATAAAATATCCACA
ACGGTTTAAATTTCAAATTTGAATCTGCGTGATTTCACGTGACATTACATCTGCGTAGGA
TCTACTCGAAGCCCACTAACTTGGTTTTCTGAAAACCCTTCACCCACTGGTATATAAAGTCTCCTAAAT
TTGCATTATAGTCTAGGTTTTCTGAAAACCCTTCACCCACTGGTATATAAAGTCTCCTAAAT

CTCGAAATTTCTCAGGACAATCATTCTGCTCTCTCTATAGCCTCCGTCTCTTCTCTCTCGA
CCTAACCAAGCAACGACGCAAATG (SEQ ID NO: 7)

+1 ↑

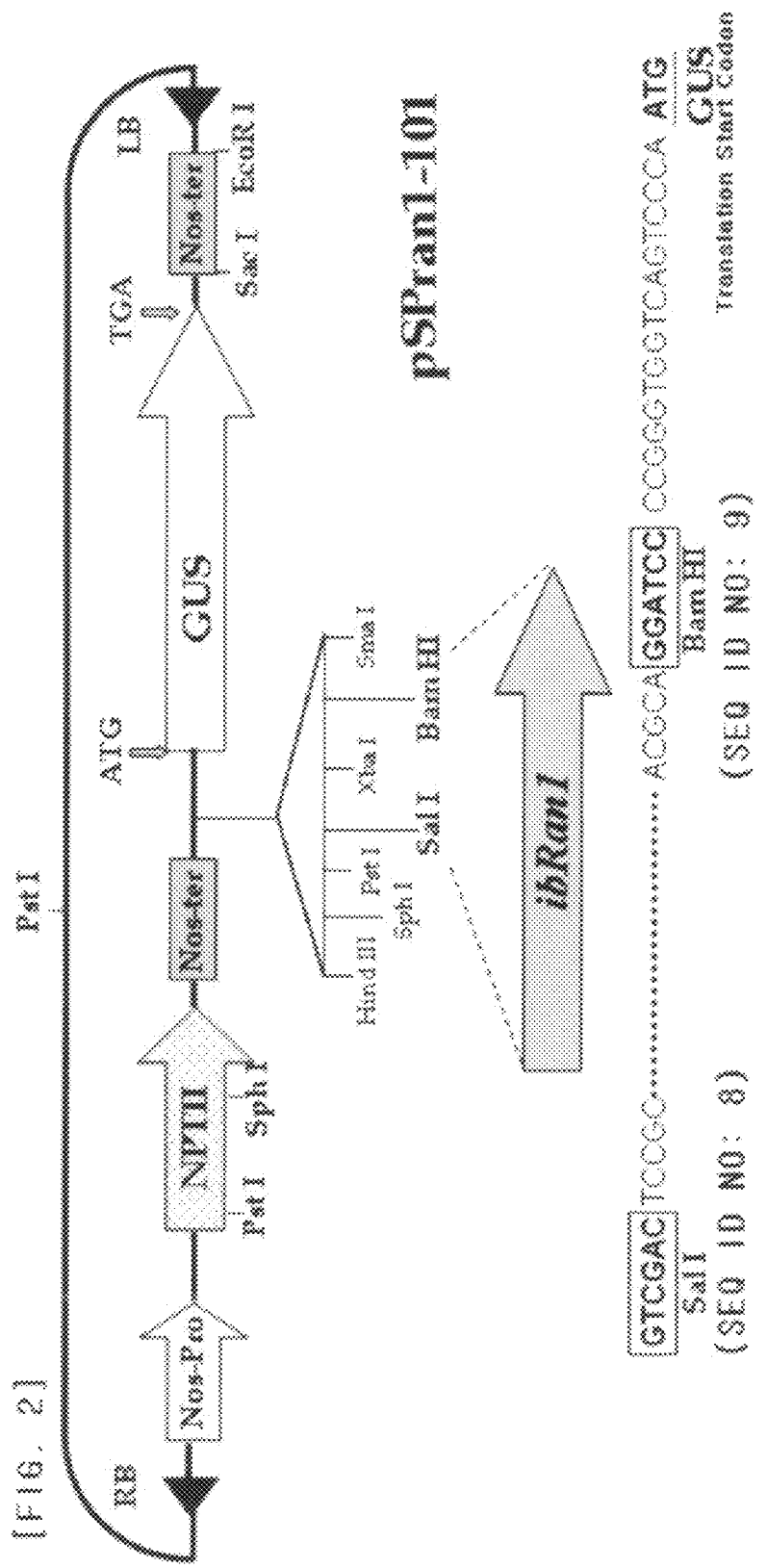

[FIG. 3]

pSPran1-221

...ACCCAGGATCCCCGGGGTGGTCAGTCCCA ATG
        BamHI                    GUS
                                  Translation Start Codon (SEQ ID NO: 9)

GCATGCTCCGC......
SphI (SEQ ID NO: 10)

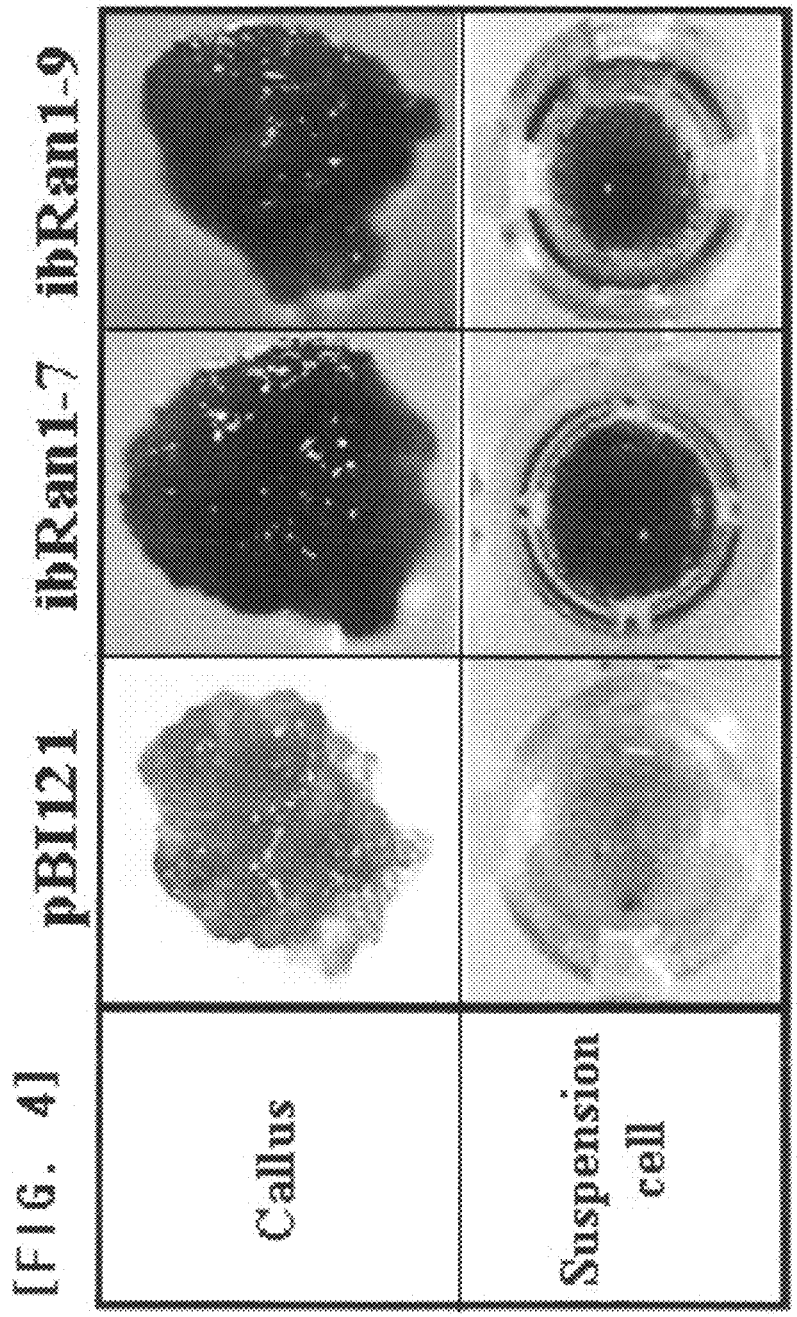
[FIG. 4]

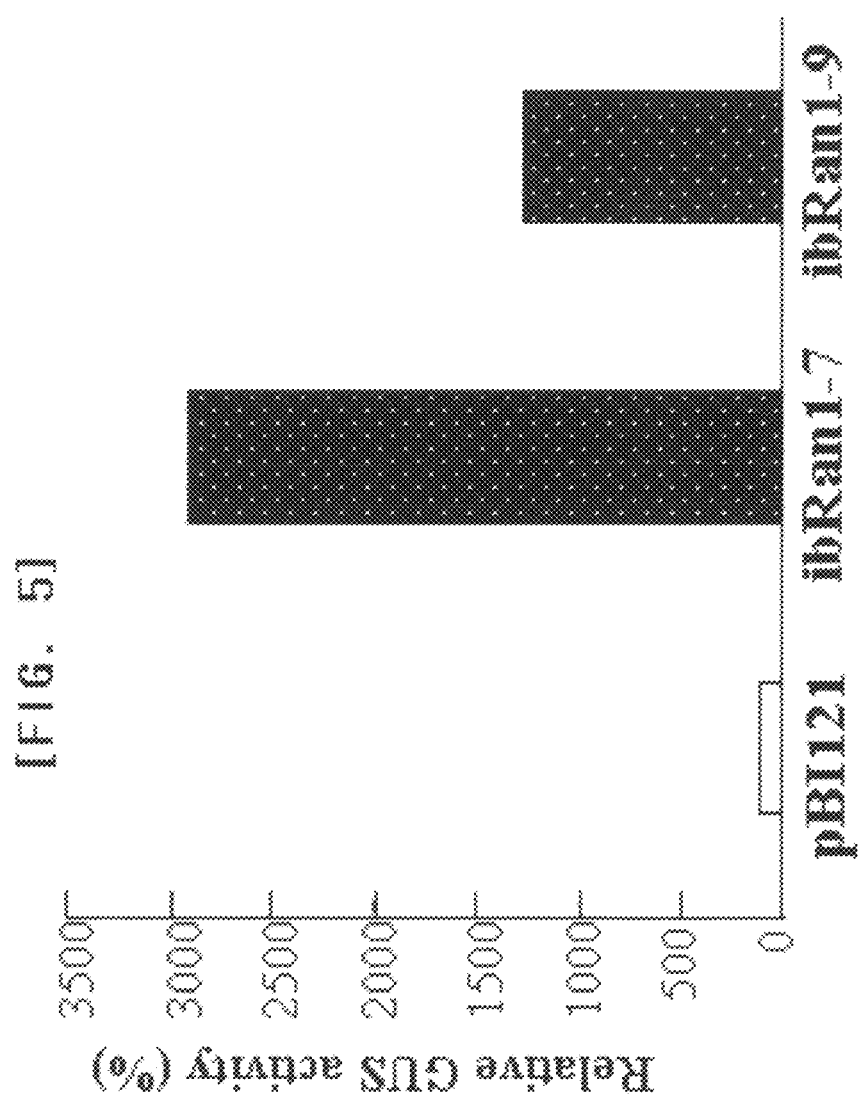
[FIG. 5]

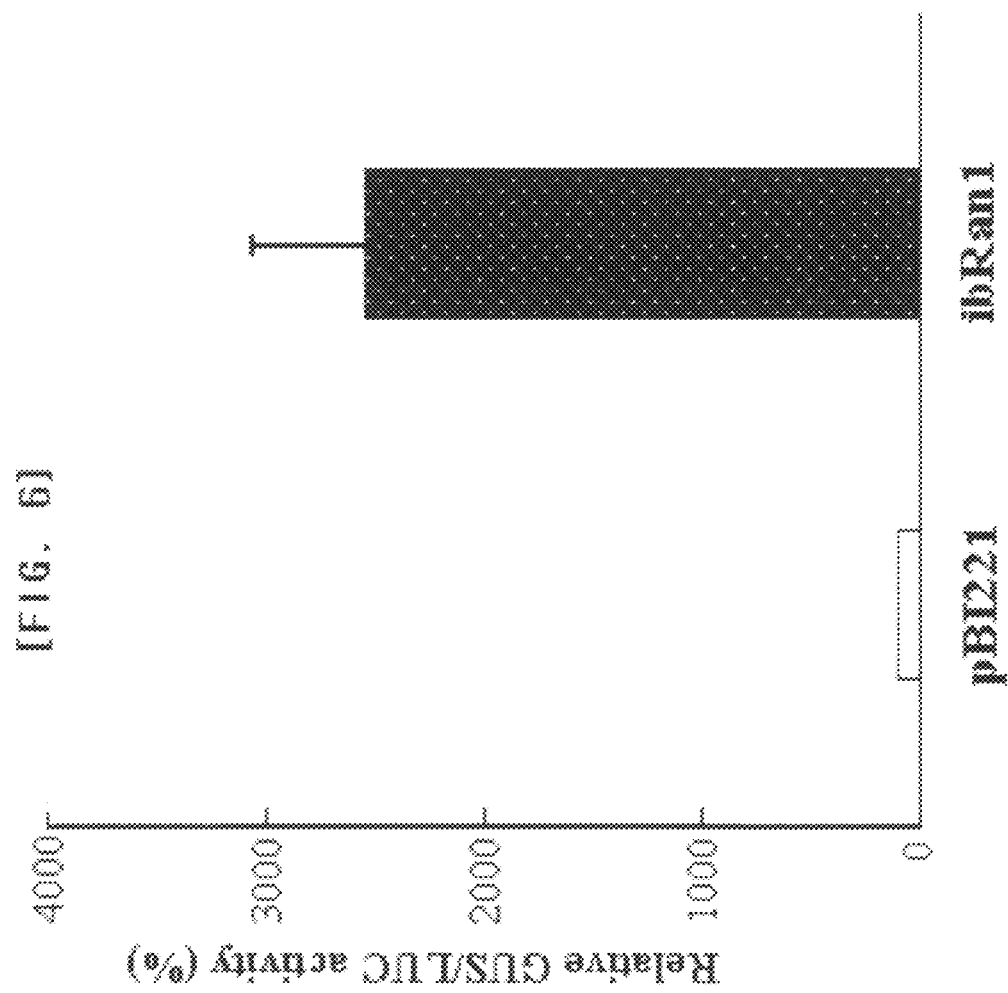

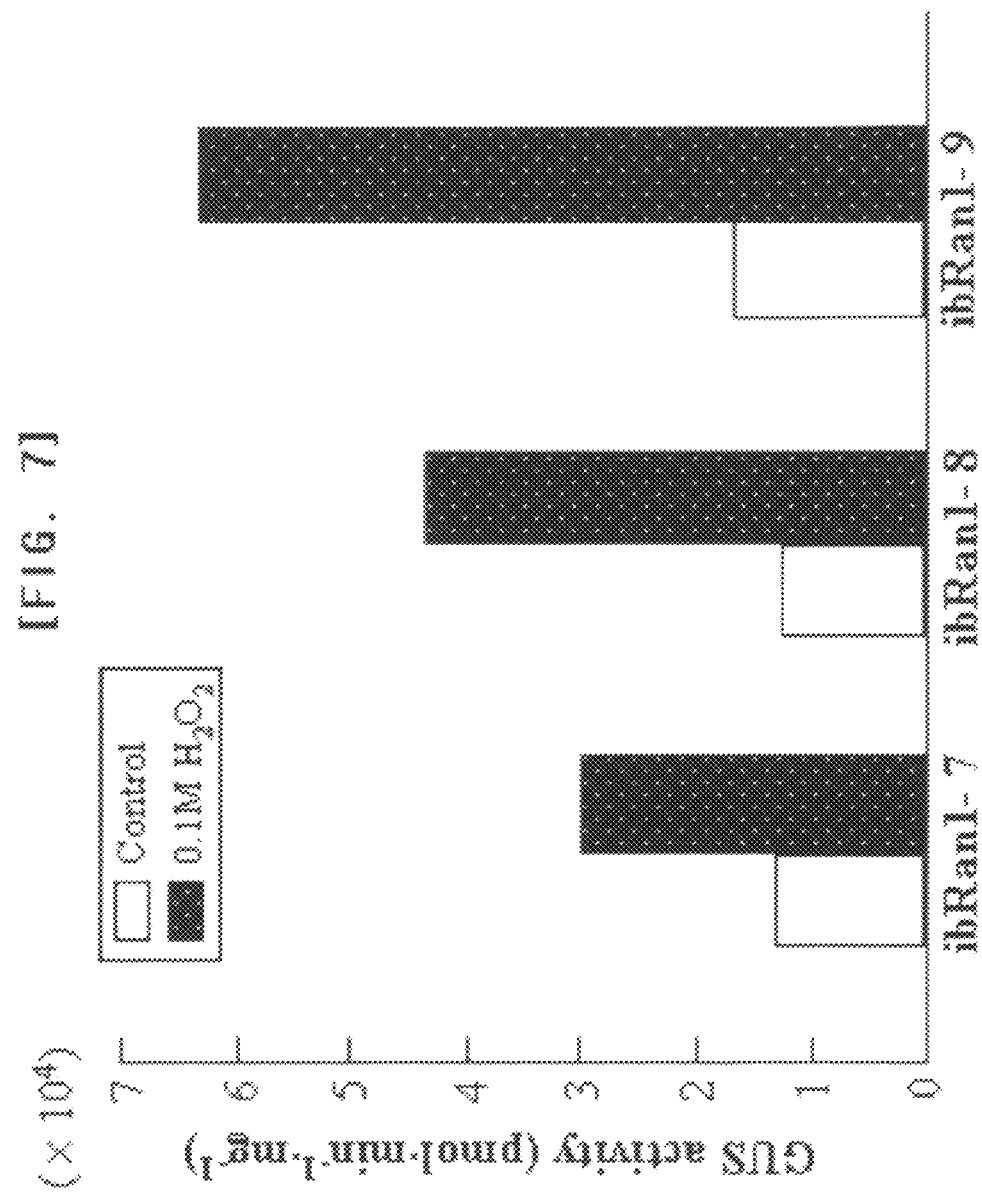
[FIG. 7]

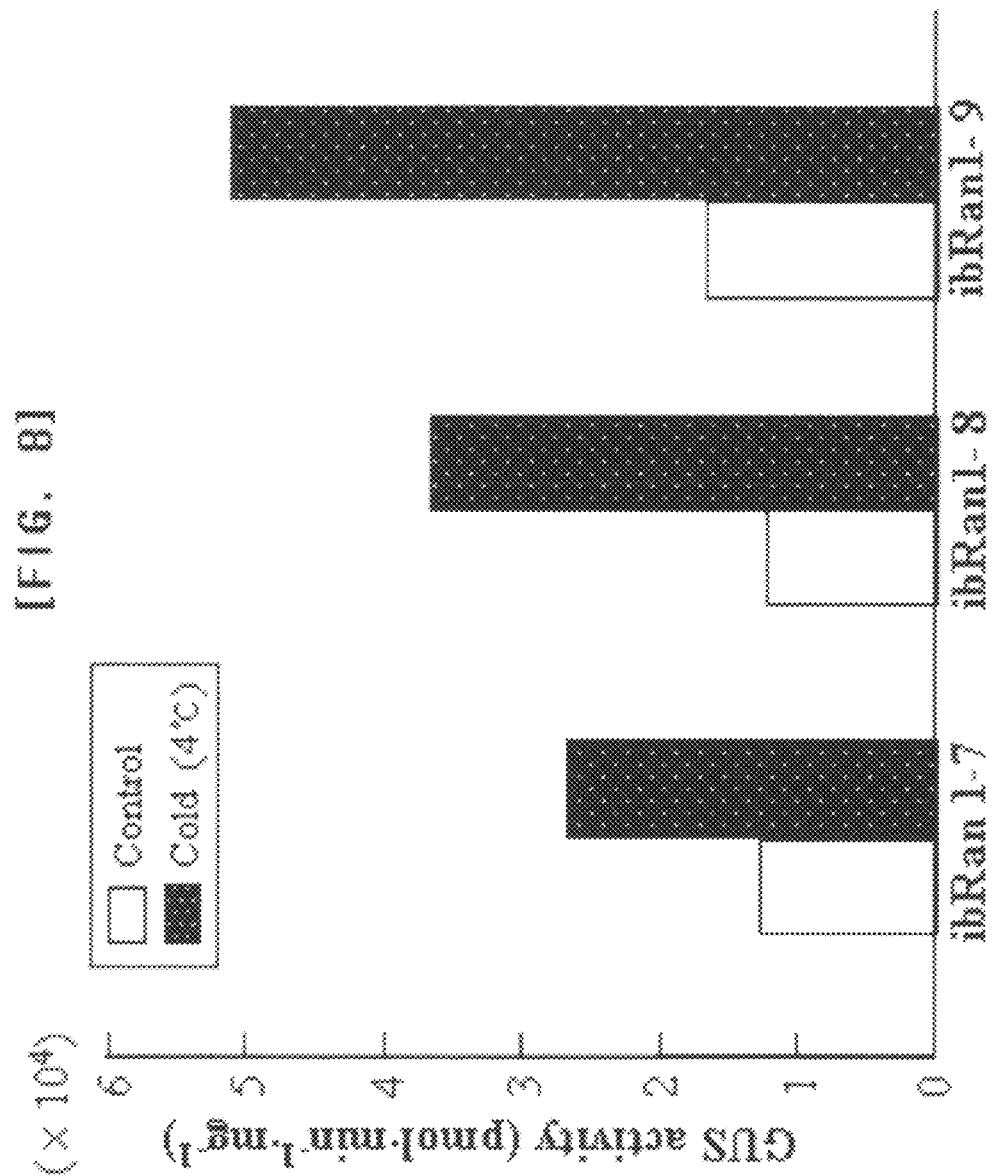
[FIG. 8]

[FIG. 9]
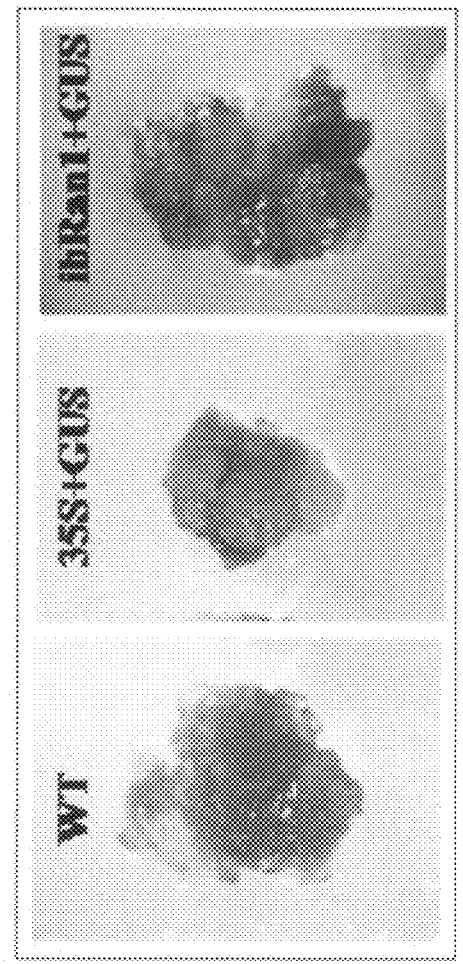
Embryogenic Callus
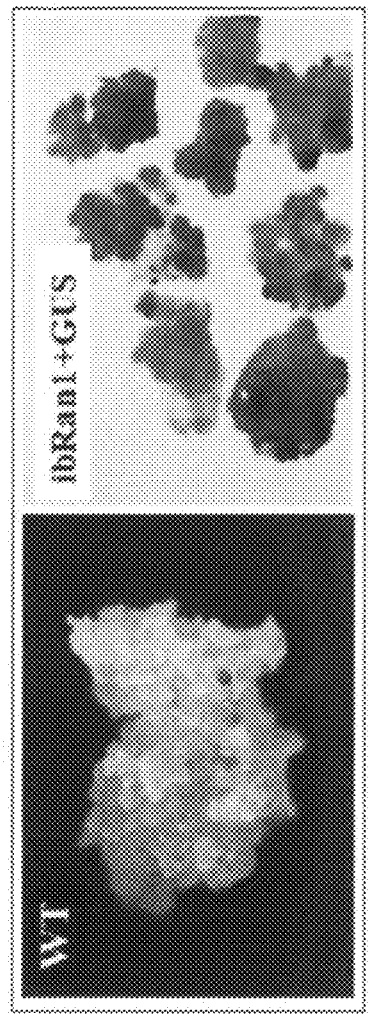
Nonembryogenic Callus

SEQUENCE LISTING

<160> NUMBER OF SEQ ID NOS: 10

<210> SEQ ID NO 1
<211> LENGTH: 1348

```
<212> TYPE: DNA
<213> ORGANISM: Ipomoea batatas cv Yulmi

<400> SEQUENCE: 1
aacacatggg gttggaggaa caaagttaac tgatagccgt tacaattatt acaaccgtcc      60
gcttcacttg agagcgtttg ggttgggcta tgaactacta aaatatctgt tctaacttat     120
tcttgtataa atagtttatg cccttgcctt gtagggcta tgaattacta aaatatctgt      180
tgaacttatt cttgtttaaa tagtcttatt cgtcaatttt ctttaatctt ctctctctct     240
cttctctcct agttggttga caaaaactcc aaaaaaaaaa aaaacaatt actatttagc      300
ttgctctaac atcattgata aaagtttata gagactctat aataataatt taaagagtta    360
attccatttt ttgtcttaga tttataggtg acaattcagt tttagtcaat ttttattaaa    420
acatcctcat ttggtcctag tattactgcg gcatgactat ttttagtcct tcatcctcat   480
cgttaaatac aaatgcattt cagtctttct tatacaaagt atgttgaacc gttatatttt    540
tatgtttatt tttttgaaa acatccataa ttgaagggcc gaaacatcat tgaatttaac    600
gatatttaaa ctgttttgta aattaatgac aaaaaatggt tatgttacaa taatactagg   660
accaaaagtg aatgttctaa taaaaaagga cttatggact gccacctata aatataggac   720
caaaatgaaa ttaactctaa ttttaaattc atcacttcaa agagtataaa agtttcattg   780
gagtactatt aaacattttt ttttgttaa taaaccgtcc caaatgtaa ttttttttc      840
attcgtactt ggagaagtca tccttaagaa aaatgaagtt tatgaagaga aaaaggtcca  900
aggatgatga aaaatctaaa ttgaatccct tgtgcgtgca taaagactag aatatgttaa  960
tggattgatt acgtcactcg taatttcttt ctacagtaac tctaggacca agtcttgtga 1020
gtttaggatt aatcccaaaa aagtcaaaaa ctaaatcac ccaaatgtaa aaacaaaac    1080
aaaagaagtc tataaatgcc acaaaataaa ctaaaaataa aatatccaca acggtttaaa  1140
tttcaaaatt tgaatctgcg tgattttcac gtgacattac atctgcgtag gatctactcg 1200
aagcccacta actttgatcc gacggtccga atatcgcgtt aggctaaagc tacttgcatt 1260
atagtctagg ttttctgaaa aacccttcac ccactggtat ataaagtctc ctaaatctcg 1320
aaatttctca ggacaatcat tctgctct                                   1348

<210> SEQ ID NO 2
<211> LENGTH: 50
<212> TYPE: DNA
<213> ORGANISM: Ipomoea batatas cv Yulmi

<400> SEQUENCE: 2
ctctatagcc tccgtctctt tctctctcga cctaaccaag caacgacgca                50

<210> SEQ ID NO 3
<211> LENGTH: 30
<212> TYPE: DNA
<213> ORGANISM: Artificial Sequence
<220> FEATURE:
<223> OTHER INFORMATION: PCR PRIMER

<400> SEQUENCE: 3
acgcgtcgac tccgcttcac ttgagagcgt                                      30

<210> SEQ ID NO 4
<211> LENGTH: 28
<212> TYPE: DNA
<213> ORGANISM: Artificial Sequence
<220> FEATURE:
<223> OTHER INFORMATION: PCR PRIMER
```

<400> SEQUENCE: 4
cgggatcctg cgtcgttgct tggttagg                                           28

<210> SEQ ID NO 5
<211> LENGTH: 28
<212> TYPE: DNA
<213> ORGANISM: Artificial Sequence
<220> FEATURE:
<223> OTHER INFORMATION: PCR PRIMER

<400> SEQUENCE: 5
acatgcatgc tccgcttcac ttgagcgt                                           28

<210> SEQ ID NO 6
<211> LENGTH: 28
<212> TYPE: DNA
<213> ORGANISM: Artificial Sequence
<220> FEATURE:
<223> OTHER INFORMATION: PCR PRIMER

<400> SEQUENCE: 6
cgggatcctg cgtcgttgct tggttagg                                           28

<210> SEQ ID NO 7
<211> LENGTH: 1401
<212> TYPE: DNA
<213> ORGANISM: Ipomoea batatas cv Yulmi

<400> SEQUENCE: 7
aacacatggg gttggaggaa caaagttaac tgatagccgt tacaattatt acaaccgtcc         60
gcttcacttg agagcgtttg ggttgggcta tgaactacta aaatatctgt tctaacttat        120
tcttgtataa atagtttatg cccttgcctt gtaggggcta tgaattacta aatatctgt         180 tgaacttatt cttgttttaaa tagtcttatt cgtcaatttt ctttaatctt ctctctctct        240
cttctctcct agttggttga caaaaactcc aaaaaaaaaa aaaacaatt actatttagc         300 ttgctctaac atcattgata aaagtttata gagactctat aataataatt taaagagtta        360
attccatttt ttgtcttaga tttataggtg acaattcagt tttagtcaat ttttattaaa        420
acatcctcat ttggtcctag tattactgcg gcatgactat ttttagtcct tcatcctcat        480
cgttaaatac aaatgcattt cagtctttct tatacaaagt atgttgaacc gttatatttt        540
tatgtttatt ttttttgaaa acatccataa ttgaagggcc gaaacatcat tgaatttaac        600
gatatttaaa ctgttttgta aattaatgac aaaaaatggt tatgttacaa taatactagg        660
accaaaagtg aatgttctaa taaaaaagga cttatggact gccacctata aatataggac        720
caaaatgaaa ttaactctaa ttttaaattc atcacttcaa agagtataaa agtttcattg        780
gagtactatt aaacatttttt tttttgttaa taaaccgtcc caaatgtaa ttttttttc         840 attcgtactt ggagaagtca tccttaagaa aaatgaagtt tatgaagaga aaaaggtcca        900
aggatgatga aaaatctaaa ttgaatccct tgtgcgtgca taaagactag aatatgttaa        960
tggattgatt acgtcactcg taatttcttt ctacagtaac tctaggacca agtcttgtga       1020
gtttaggatt aatcccaaaa aagtcaaaaa ctaaatcac ccaaatgtaa aaacaaaac         1080 aaaagaagtc tataaatgcc acaaaataaa ctaaaaataa aatatccaca acggtttaaa       1140
tttcaaaatt tgaatctgcg tgattttcac gtgacattac atctgcgtag gatctactcg       1200
aagcccacta actttgatcc gacggtccga atatcgcgtt aggctaaagc tacttgcatt       1260
atagtctagg tttttctgaaa aacccttcac ccactggtat ataaagtctc ctaaatctcg       1320

-continued

```
aaatttctca ggacaatcat tctgctctct ctatagcctc cgtctctttc tctctcgacc    1380
taaccaagca acgacgcaat g                                              1401

<210> SEQ ID NO 8
<211> LENGTH: 11
<212> TYPE: DNA
<213> ORGANISM: Artificial Sequence
<220> FEATURE:
<223> OTHER INFORMATION: Synthetic construct

<400> SEQUENCE: 8
gtcgactccg c                                                         11

<210> SEQ ID NO 9
<211> LENGTH: 31
<212> TYPE: DNA
<213> ORGANISM: Artificial Sequence
<220> FEATURE:
<223> OTHER INFORMATION: Synthetic construct

<400> SEQUENCE: 9
acgcaggatc cccgggtggt cagtcccaat g                                   31

<210> SEQ ID NO 10
<211> LENGTH: 11
<212> TYPE: DNA
<213> ORGANISM: Artificial Sequence
<220> FEATURE:
<223> OTHER INFORMATION: Synthetic construct

<400> SEQUENCE: 10
gcatgctccg c                                                         11
```

PROMOTER FROM SWEET POTATO RAN GTPASE GENE FOR THE HIGH LEVEL EXPRESSION IN PLANT-TISSUE CULTURE AND VECTOR USING THE SAME

CROSS REFERENCE TO RELATED APPLICATIONS

This application is a National Stage of International Application No. PCT/KR2008/004684 filed Aug. 12, 2008 claiming priority based on Korean Patent Application No. 10-2007-0081320 filed Aug. 13, 2007, the contents of all of which are incorporated herein by reference in their entirety.

TECHNICAL FIELD

The present invention relates to a promoter of sweetpotato gene of Ran GTPase which is a kind of plant small GTP binding protein, an expression vector comprising the promoter, and a method for expressing a foreign gene in plant and plant-cell culture using the vector. More particularly, the present invention relates to a promoter of Ran GTPase gene (ibRan1) derived from sweetpotato, wherein the promoter comprise a sequence represented by SEQ ID NO.: 1 and induce high level expression in plant-tissue culture. In addition, the present invention relates to an expression vector for plant cell comprising the promoter and a method for expressing a foreign gene in plants and plant tissue cultured cells such as cultured roots using the vector.

BACKGROUND ART

Recently, the development of plant biotechnology makes it possible to produce a transgenic plant. The technology for producing the transgenic plant can used in the two aspects. First aspect, it makes it possible to produce a valuable plant with new function which cannot be produced by conventional breeding technology. Second aspect, it makes it possible to use a plant as bioreactor. In other words, it makes it to produce valuable proteins and physiologically active substances derived from plant or animal using the transgenic plant or the transgenic plant cell line (Doran P M., 2000 Biochem. Engineering 11:199-204).

Many advantages of producing the useful proteins in the transgenic plant cell lines compared with the animal cell culture are as follows:

1) confirmation of security from infections of animal viruses 2) cheap culture cost in that the cost of plant cell culture can be reduced to 1/30 of animal cell culture's cost or 1/3 of microorganism culture's cost.

Thus, the studies for producing the useful proteins using transgenic cell lines as bioreactor have been increased rapidly. But the related study could be available practically only if the production protein of introduced gene reaches to a content of economic efficiency. The protein content produced in the transgenic plants or cell lines was only 0.001-0.4% out of total water-soluble protein contents excepting for Phytase (14.4%) and Xylanase (4.1%). Thus, most results of the studies are not available in the aspect of economic efficiency.

Another successful cases associated with the plant cell culture techniques are the production of secondary metabolites such as Shikonin (Japan Mitsui Petrochemical Industries Ltd.) and Taxol (Samyang Genex). But these cases have been limited to enhance the productivity of plant-originated substances. Recently as the genes related to these bioactive substances have begun to be found, the necessity of the development of molecular farming to enhance the expression of genes related to pathway of these bioactive substances has been noticed (Goossen et al., 2003 PNAS 100:8595-8600). Recently the gene related to pathway of the saponin biosynthesis, the medicinal component of ginseng have been found (Han et al., 2006 Plant Cell Physiol. 47:1653-1662; Tansakul et al., 2006 FEBS 580:5143-5149), thus there has been a need for generation of ginseng cultured roots with high saponin content using the metabolic engineering.

Consequently, the studies for promoters regulating the expression levels of foreign genes play a key role in the mass-production of the useful proteins originated from plant or animal and in high level expression of genes related to pathway for secondary metabolites using the plant tissue-culture.

Thus in order to develop these promoters, the important aspects to be considered are as follows:

1) the expression levels of foreign genes inserted into transformants are to be regulated. The genes for transformation can be used diversely according to the target characters. Therefore the expression levels of the genes are to be required variously. In order to accumulate the secondary metabolites in cultured cells, it is advantageous to induce high level expression of genes related to the biosynthesis pathway for the production of the physiological active substances. In order to produce useful proteins in a large quantities, it is required to develop the high-expressing promoter in the logarithmic growth phase, whereas in order to accumulate secondary metabolites in a large quantities, it is required to develop the high-expressing promoter in the stationary phase. Consequently, in order to regulate the expression levels of foreign genes minutely, promoters having diverse expression levels should be developed.

2) The promoters for transformation are to be protected by intellectual properties. At present the universal promoter, CaMV 35S promoter (Patent No. JP19931172-A1) have been patented. Therefore, if the useful substances are produced in a large quantities using the transformant lines containing the CaMV 35S promoter, the royalty have to be paid and the profitability decreases rapidly.

3) It is necessary to develop the suitable promoters for versatile tissue cultured cell lines. Tobacco BY-2 cell (*Nicotiana tobacum* L. cv.) has comparatively rapid growth rate and is the most suitable cell line for production recombinant proteins. But it was also reported that the medicinal proteins could be produced in the suspension cells of the soybean, tomato, and rice, and the hairy roots of tobacco.

For example, the productivity of human granulocyte-macrophage colony stimulating factor (hGM-CSF) using inducible promoter (amylase expression system) in rice cell lines was much higher than using the constitutive promoter, CaMV 35S in the tobacco cell lines (Shin et al., 2003 Biotech. and Bioengineering 82:778-783). In case that medicinal components exist in the roots such as ginseng, the promoter expressing highly in the cultured roots is needed. Thus in order to produce the useful proteins it is required to develop cell lines and promoters suitable for them respectively on a case-by-case basis.

Most of the root crops such as ginseng, Chinese bellflower and Lance Asiabell (*Codonopsis lanceolata*) are edible and have good pharmacological effects to be valuable crops. However, most of root crops are perennial (4~6 years) and have long growth periods. The worse is difficult to extract DNA and RNA of root crops because they contain a lot of polysaccharides. It is also difficult to monitor the growth of storage roots growing up in the underground. Thus molecular breeding technology for the root crops has hardly been studied.

However, as genes related to bioactive substances have been begun to be reported recently, it have been required to develop the expression system for enhancement of the genes expression related to these biosynthesis pathway and accumulation bioactive substances in a large quantities.

Medicinal root crops comparatively require long cultivation periods so that it needs long time and high cost for producing and manufacturing economically.

Therefore, it is very important to develop the technology of molecular farming in the basis of study for promoters which can accumulate useful bioactive substances (for example saponin) in a short period and in a large quantities using the cultured roots and cultured cells.

Consequently, for the mass-producing useful foreign proteins and bioactive substances in an efficient and economic way using the plant tissue culture, the promoters directing high level expression of a foreign gene in tissue cultured cells such as cultured roots should be studied.

Meanwhile, it have been reported that Ran (Ras-related nuclear protein) GTPase is a protein present abundantly at meristematic tissues such as embryos in a developmental stage and suspension cultured cells. It plays a major role in regulation of cell growth and cell proliferation, and is essential for the translocation of RNA and proteins through the nuclear pores complex. In animal, Ran GTPase plays a key role in regulating nuclear processes through cell mitosis together with Ran-binding protein (RanBPs), RCC1 (a GEF, RanGEF) and RanGAP (a GAP) regulating these proteins.

Four kinds of Ran GTPase (AtRAN1, AtRAN2, AtRAN3, AtRAN4) derived from *Arabidopsis* have been identified through comparing the similarity of nucleotide sequences. There was a note that AtRAN4 of them could be induced by salt stress, but related result has not been reported yet. In addition, cDNA of Ran GTPase expressed highly in the roots of soybeans has been isolated. Ran GTPase cDNA has been identified from all tissues of tomatoes such as leaves (cotyledon, young leaves and senescencing leaves) of versatile stages of development, as well as roots and fruits. It has been found that Ran GTPase cDNA of tomato is a kind of nucleoprotein and suppresses the pim1 mutation of *S. pombe* (Robert et al., 1994 91:5863-5867).

But it has not been found how these various proteins translocate into the target places after synthesized or by what mechanism they are expressed in special tissues. The promoter of Ran GTPase gene in plants has been hardly studied.

DISCLOSURE OF INVENTION

Technical Problem

Accordingly, the present invention has been made keeping in mind the above problems occurring in the prior art, and an object of the present invention is to provide the promoter derived from sweetpotato Ran GTPase gene(ibRan1), directing high level expression of a foreign gene in plant tissue cultured cells.

It is another object of the present invention to provide a vector directing high level expression of a foreign gene in plant tissue cultured cells, comprising a promoter derived from sweetpotato Ran GTPase gene (ibRan1) and a 5'-untranslated region of the gene.

It is a further object of the present invention to provide a expression vector resistant against stress, comprising a promoter induced by stress and a 5'-untranslated region of the gene.

It is a still further object of the present invention to provide a method for inducing high level expression of a foreign gene in the plant tissue cultured cells using the expression vector to produce useful proteins in a large quantities with the plant tissue cultured cells such as cultured roots.

Technical Solution

In accordance with an aspect of the present invention, there is provided an isolated promoter of a Ran GTPase gene (ibRan1), comprising a nucleotide sequence of SEQ ID NO.: 1.

The promoter is used for generation a transformant mass-producing bioactive substances.

The promoter is used for generation a transformant resistant to stress.

In accordance with another aspect of the present invention, there is provided an isolated 5'-untranslated region of a Ran GTPase gene (ibRan1), comprising a nucleotide sequence of SEQ ID NO.: 2.

In a still another aspect, the present invention provides a binary vector for transforming plants, wherein the vector comprises a promoter of a Ran GTPase gene(ibRan1) comprising a nucleotide sequence of SEQ ID NO.: 1. and a 5'-untranslated region of a Ran GTPase gene(ibRan1) comprising a nucleotide sequence of SEQ ID NO.: 2.

In still a further aspect, the present invention provides a transient expression vector, wherein the vector comprises a promoter of a Ran GTPase gene(ibRan1) comprising a nucleotide sequence of SEQ ID NO.: 1. and a 5'-untranslated region of a Ran GTPase gene(ibRan1) comprising a nucleotide sequence of SEQ ID NO.: 2.

In yet another aspect, the present invention provides a transformant transformed with the isolated promoter or with the binary vector.

In yet another aspect, the present invention provides a transformant transformed with the transient expression vector.

In yet another aspect, the present invention provides a transgenic plant transformed with the isolated promoter or with the binary vector.

In yet another aspect, the present invention provides a tissue cultured cell line transformed with the isolated promoter or with the binary vector.

In yet another aspect, the present invention provides a method expressing a foreign gene in plant tissue cultured cell transformed with the isolated promoter or with the binary vector.

In yet another aspect, the present invention provides a PCR primer suitable for amplifying a DNA fragment comprising the nucleotide sequence of SEQ ID NO.:1 and 2, the primer being represented by a nucleotide sequence as shown in SEQ ID NO.: 3 or 4.

In a final aspect, the present invention provides a PCR primer suitable for amplifying a DNA fragment comprising the nucleotide sequence of SEQ ID NO.:1 and 2, the primer being represented by a nucleotide sequence as shown in SEQ ID NO.: 5 or 6.

Advantageous Effects

The present invention provides the promoter and 5'-untranslated region of sweetpotato gene of Ran GTPase which is small GTP binding protein. The promoter and 5'-untranslated region according to the present invention can induce high level expression of a foreign gene in plant tissue cultured cells such as calluses and suspension cultured cells, resulting that the activity of the present invention promoter is average 15.5 times higher than that of universal promoter, CaMV 35S promoter. In addition, it has been identified that the promoter of ibRan1 gene has very strong activity in the transient expression assay using the BY-2 cell line.

In addition, the present invention promoter can be highly induced by cold and oxidative stresses.

Therefore, the present invention is very useful in mass-production of useful proteins and with the plant tissue cultured cells and in the generation of transgenic plants resistant to stresses.

BRIEF DESCRIPTION OF THE DRAWINGS

The patent or application file contains at least one drawing executed in color. Copies of this patent or patent application publication with color drawings will be provided by the Office upon request and payment of the necessary fee.

The above and other objects, features and other advantages of the present invention will be more clearly understood from the following detailed description taken in conjunction with the accompanying drawings, in which:

FIG. 1 is a view showing the sequences of promoter for high level expression in plant-cell culture and 5'-untranslated region of a Ran GTPase gene(ibRan1) derived from sweetpotato;

FIG. 2 is a schematic diagram showing the structure of a binary vector (hereinafter referred to pSPran1-101) for transforming plants comprising a promoter for high level expression in plant-cell culture and a 5'-untranslated region of a sweetpotato Ran GTPase gene(ibRan1) according to the present invention;

FIG. 3 is a schematic diagram showing the structure of a transient expression vector (hereinafter referred to pSPran1-221) for transforming plants comprising a promoter for high level expression in plant-cell culture and a 5'-untranslated region of a sweetpotato Ran GTPase gene(ibRan1) according to the present invention;

FIG. 4 is a view showing the expression pattern of GUS in callus transformed with pSPran1-101 vector of the present invention using the histochemical staining assay.

FIG. 5 is a view showing the high level expression of promoter in suspension cultured cell transformed with pSPran1-101 vector of the present invention using the quantitative analysis method for GUS.

FIG. 6 is a view showing the result of a transient assay in BY-2 cell using pSPran1-221 vector according to the present invention.

FIG. 7 is a view showing that the promoter of the present invention is induced by reactive oxygen stress, by treating tobacco plants transformed using pSPran1-101 with $H_2O_2$.

FIG. 8 is a view showing that the promoter of the present invention is induced by cold stress, by treating tobacco plants transformed using pSPran1-101 with cold.

FIG. 9 is a view showing the expression pattern of GUS in ginseng callus transformed with pSPran1-101 vector of the present invention using the histochemical staining assay.

BEST MODE FOR CARRYING OUT THE INVENTION

Figure 10:
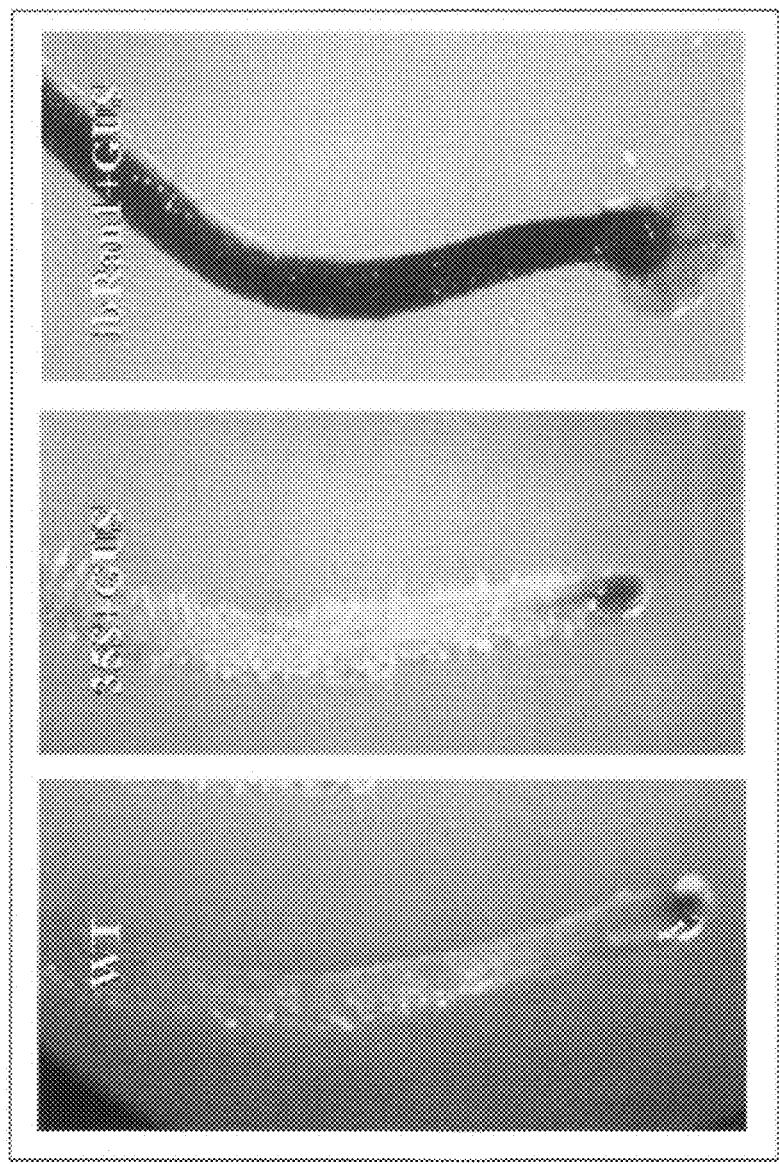
FIG. 10 is a view showing the expression pattern of GUS in ginseng adventitious root transformed with pSPran1-101 vector of the present invention using the histochemical staining assay.

In order to accomplish the objects, the present inventors succeeded in cloning a high level expression promoter for tissue cultured cells, derived from a sweetpotato gene(ibRan1) of Ran GTPase that is a kind of small GTP binding protein. Then the present inventors constructed a binary vector for plant cell transformation and a transient vector, carrying the promoter and 5'-untranslated region and found that the promoter has high specificity for tissue cultured cells, particularly cultured roots and high level of stress inducibility using expression assay of the vectors.

More particularly, the present inventors have constructed the EST library and identified 1431 high quality ESTs sequences using suspension cultured cell of sweetpotato which is a typical root crop and has been studied in the field of related molecular biology techniques. The 1431 ESTs derived from suspension cultured cell of sweetpotato have been compared and analyzed with dbESTs of sweetpotato leaves and roots. The result has been found that five ESTs (cinnamyl-alcohol dehydrogenase, glyceraldehyde-3-phosphate dehydrogenase, cyclophilin, GTP binding nuclear protein Ran etc) were selected as the most abundant genes in the sweetpotato suspension cultured cell. The five ESTs selected have been identified using the Northern analysis (Kim et al., 2006 J. Plant Biol., 49:364-370).

The present inventors have finally screened Ran GTPase (Ras-related nuclear protein) that express from initial phase to logarithmic growth phase of suspension cultured cell among five ESTs and initially cloned the promoter of Ran GTPase gene from root crops, thus developing a high level expression promoter for suspension cultured cells. It have been found that the promoter of Ran GTPase gene according to the present invention is highly expressed in the tissue cultured cells including the cultured roots such as ginseng cultured roots.

In one aspect, therefore, the present invention provides an isolated promoter for the high level expression in plant cultured cell, comprising a nucleotide sequence of SEQ ID NO.: 1 and an isolated 5'-untranslated region of a sweetpotato Ran GTPase gene(ibRan1), comprising a nucleotide sequence of SEQ ID NO.: 2.

The DNA sequence of the promoter of SEQ ID NO.: 1 is derived from the region of by −1 to −1348 relative to the transcription initiation site of the sweetpotato Ran GTPase (ibRan1) (FIG. 1). The promoter according to the present invention can induce high level expression of target genes in plant tissue cultured cells and can be strongly induced by stresses.

The untranslated region of SEQ ID NO.: 2 is derived from the region of by +1 to +50 relative to the transcription initiation site of the sweetpotato Ran GTPase(ibRan1) (FIG. 1).

In accordance with another aspect, the present invention provides a vector for transforming plants (pSPran1-101) and a transient expression vector (pSPran1-221) and the two kinds of vector comprise high level expression promoter for the plant tissue cultured cell and 5'-untranslated region of Ran GTPase gene(ibRan1) (FIGS. 2 and 3).

The high level expression vector for transforming plants is a binary vector capable of permanently expressing an foreign gene in plants and the transient expression vector is a vector capable of transiently expressing an foreign gene in plants.

Concerning the high level expression vector for plant tissue cultured cells according to the present invention, the promoter and 5'-untranslated region of Ran GTPase(ibRan1) of the present invention are located in front of the foreign gene in the pBI101 and pBI221 vector. The present invention provides the pSPran1-101 and pSPran-221 (FIGS. 2 and 3) prepared by inserting the promoter and 5'-untranslated region of Ran GTPase(ibRan1) into vector (pBI101 and pBI221) containing the GUS reporter gene. However, the GUS reporter gene is a foreign gene and may be replaced with other foreign genes which is deemed useful. In addition, it should be understood by those skilled in the art that any other plant vector can be used instead of the pBI101 and pBI221.

In accordance with still a further aspect, the present invention provides a transgenic plant tissue cultured cells such as cultured roots and plants transformed with the high level expression binary vector for plant tissue cultured cells according to the present invention. In addition, the present invention provides a plant tissue cultured cells transformed transiently with the transient expression vector according to the present invention.

The binary vector for plant tissue cultured cells may be introduced into plants or cells using *Agrobacterium* or a gene gun etc. In an embodiment of the present invention, a tobacco and ginseng was transformed using *Agrobacterium*.

The transient expression vector for plant tissue cultured cells may be introduced into cells using polyethylene glycol method or electroporation etc. In an embodiment of the present invention, a BY-2 cell was transformed using polyethylene glycol method.

The target genes for the production of foreign proteins may located next to the promoter and 5'-untranslated region of the sweetpotato Ran GTPase gene(ibRan1) in the high level expression vectors according to the present invention and may be expressed fused with the reporter gene if necessary.

In accordance with still another aspect, the present invention provides primers for the PCR amplification of DNA fragment comprising the high level promoter for plant tissue cultured cells according to the present invention, which are respectively represented by SEQ ID NO.: 3~SEQ ID NO.: 6.

MODE FOR THE INVENTION

The following examples will enable those skilled in the art to more clearly understand how to practice the present invention. It is to be understood that, while the invention has been described in junction with the preferred specific embodiments thereof, that which follows is intended to illustrate, not to limit the scope of the invention. Other aspects of the invention will be apparent to those skilled in the art to which the invention pertains.

Example 1

Cloning for the Promoter of Ran GTPase Gene(ibRan1) Expressed Highly in Suspension Cultured Cell of Sweetpotato The promoter of Ran GTPase gene(ibRan1) from sweetpotato (*Ipomoea batatas* cv White Star) was sequenced and identified by determining the sequence of 5' region of Ran GTPase gene(Kim et al., *J. Plant Biol.*, 2006, Vol 49, 364-370).

The cloned sequence of the promoter was registered in GenBank, with Accession no. EF119214 (FIG. 1). FIG. 1 shows sequences of high level expression promoter for tissue cultured cell including cultured-root and 5'-untranslated region of sweetpotato Ran GTPase gene(ibRan1) according to the present invention. In FIG. 1, the start codon 'ATG' of protein synthesis is underlined and indicated with bold letters. Base 'C' of transcription initiation site is indicated '+1'.

Example 2

Analysis for the Promoter of Ran GTPase Gene(ibRan1) Expressed Highly in Suspension Cultured Cell of Sweetpotato The promoter cloned in example 1 is comprised of sequence represented SEQ ID NO.: 1 which is upstream from transcription initiation site to −1348 bp (FIG. 1). The cis-acting elements of Ran GTPase gene(ibRan1) promoter were analysed using PLACE (A database of Plant cis-acting Regulatory DNA elements).

The result of sequence analysis indicated that ibRan1 promoter has regulatory element region of eukaryotic promoter. There is TATA box (TATAAA) for transcription initiation at −49/−44 and CAAT box (CAAT) at −174/−171, −701/−698, −942/−939, −957/−954, −1063/−1060, −1135/−1132, −1306/−1303. In addition there is binding sites for many transcription regulatory protein related to the stress in plant. ACGT motif is located at −180/−176 and −378/−375 in two discrete portions. ACGT motif is known to be related to regulate a gene that rapidly responds to stress such as drought (Nakashima K, et al., 2003 Plant J. 33, 259-307). G box (CACGTG) related to plant defense mechanism is located at one region and GT-1 box (GRWAAW/GAAAAA) is located at five regions. Also LTRE (CCGAAA/CCGAC) known as regulating factor responding to cold stress is found.

Example 3

Construction of High Level Expression Vector for Generation of Transformant and Transient Expression Vector The promoter (SEQ ID NO.: 1) cloned in example 1 and 50 bp 5' untranslated region (SEQ ID NO.: 2) of sweetpotato (*Ipomoea batatas* cv Yulmi) gene(ibRan1) of Ran GTPase, small GTP binding protein were inserted in a pBI101 and pBI221 (Clonetech) in order to construct a high level expression vector for plant tissue cultured cell and a transient expression vector respectively.

For construction of vector for high level expression in tissue cultured cell, first the high level expression promoter of SEQ ID NO.: 1 cloned in example 1 and 50 bp 5' untranslated region of SEQ ID NO.: 2 of sweetpotato gene(ibRan1) of Ran GTPase, small GTP binding protein was amplified using PCR primers shown in Table 1 and restricted by Sal I and BamH I. Then they were inserted into Sal I and BamH I sites of pBI101. The vector was named pSPran1-101 (FIG. 2).

In the PCR, conditions included the following: 94° C. for 5 min; then 30 cycles of at 94° C. for 1 min, at 62° C. for 2 min, at 72° C. for 2 min; and a final extension step of 7 min at 72° C.

TABLE 1

| | |
|---|---|
| 5' primer 5'-ACG C<u>GT CGA C</u>TC CGC TTC ACT TGA GAG CGT-3' | SEQ ID NO.: 3 |
| 3' primer 5'-CG<u>G GAT CC</u>T GCG TCG TTG CTT GGT TAG G-3' | SEQ ID NO.: 4 |

In FIGS. 2 and 3, GUS is a gene encoding 13-glucuronidase II and NPTII is a marker gene which confers kanamycin resistance. Nos-pro and Nos-ter are a promoter and a terminator for plant expression of NPTII respectively. GUS reporter gene is expressed by ibRan1 gene promoter and Nos-ter (Nopalin synthase terminator) in plants.

In addition, for construction of transient expression vector, the sweetpotato promoter of SEQ ID NO.: 1 cloned in example 1 and 50 bp 5' untranslated region of SEQ ID NO.: 2 of sweetpotato gene(ibRan1) of Ran GTPase, small GTP binding protein was amplified using PCR primers shown in Table 2 and restricted by Sph I and BamH I. Then they were inserted into Sph I and BamH I sites of pBI221. The vector was named pSPran1-221 (FIG. 3).

In the PCR, conditions included the following: 94° C. for 5 min; then 30 cycles of at 94° C. for 1 min, at 62° C. for 2 min, at 72° C. for 2 min; and a final extension step of 7 min at 72° C.

TABLE 2

| 5' primer | 5'-ACA TGC ATG CTC CGC TTC ACT TGA GCG T-3' | SEQ ID NO.: 5 |
|---|---|---|
| 3' primer | 5'-CGG GAT CCT GCG TCG TTG CTT GGT TAG G-3' | SEQ ID NO.: 6 |

Example 4

Construction of Tobacco Transformant Using pSPran1-101 Vector According to the Present Invention The pSPran1-101 vector constructed in Example 3 was introduced into *Agrobacterium tumefaciens* GV3101 using a freeze-thaw method (An, G. 1987, Methods in Enzymology).

The *Agrobacterium* carrying the gene of interest on the vector was cultured at 28° C. for 2 days with agitation and then a leaf of tobacco (*Nitoana tobacum*, Xanthi) was soaked into the *Agrobacterium* culture fluid so as to construct tobacco transformant.

Example 5

Establishment of Suspension Cultured Cell Lines Carrying a High Level Expression Promoter from Screened Transformant According to the Present Invention Seeds were harvested from the tobacco transformants prepared in Example 4 and plated on tissue culture MS medium with 30 mg/L Kanamycin. Then transformants resistant to Kanamycin were screened and seeds were harvested from the transformants (F1 and F2).

To analyse the activity of ibRan1 promoter in suspension cultured cell, calluses were induced from leaves of screened transformants (F2). Then suspension cultured cell lines were induced from the calluses. In detail, F2 seeds sterilized were germinated in MS selection medium containing Kanamycin to induce the callus. After seeds were cultivated for 2-3 weeks, leaf segments were excised and cultivated on callus induction medium containing hormone(3% sucrose, 2 mg/L naphthaleneacetic acid (NAA), 0.25 mg/L 6-benzylaminopurine (BA), 0.4 mg/L thiamine HCl, 0.5% phytoagar).

After leaf segments were cultivated for about 2-3 weeks, calluses were induced. The activity of GUS in calluses induced from the cotyledon explants of F2 was analysed using the histochemical staining method. To stain each transformed callus tissues, each tissue of callus was soaked in the solution containing 1 mM X-gluc (5-bromo-4-chloro-3-indolyl-β-glucuronide), 100 mM sodium phosphate (pH 7.0), 10 mM EDTA, 0.5 mM potassium ferricyanide, 0.5 mM potassium ferrocyanide, and 0.1% Triton X-100 and reacted for at 37° C. 16 hours.

As shown in FIGS. 4 and 5, pBI121 (Clontech, USA) containing CaMV 35S promoter was used as control. In FIG. 4, it was identified that GUS showed high level activity in tobacco (ibRan1-7, ibRan1-9) callus tissues transformed with pSPran1-101, whereas GUS showed low level activity in tobacco callus tissue transformed with pBI121 used universally.

After the activity of GUS in the callus was identified, the callus was divided into many pieces and transferred into suspension culture medium (3% sucrose, 2.7 mM $KH_2PO_4$, 181 µg/L 2,4-D, 1 mg/L thiamine HCl) to induce suspension culture cell line at 100 rpm, 25° C. Then cell samples were taken from the induced suspension culture cell line and treated by GUS staining method (FIG. 4). At the same time, the GUS activity of the samples was measured by enzyme method using MUG (4-methylumbelliferyl glucuronide) substrate(Jefferson et al., 1987 EMBO J. 6: 3901-3907) (FIG. 5).

The transformed suspension cultured cell lines, ibRan1-7 and ibRan1-9 containing promoter of sweetpotato ibRan1 gene showed the high level promoter activity which is 29 times or 12 times higher than the promoter activity of the transformed suspension cell cultured line containing the universal promoter CaMV 35S (FIG. 5).

Example 6

Transient Assay of ibRan1 Promoter Using the Protoplast of BY-2 Cell Line

The transient assay of ibRan1 promoter was carried out using the protoplast of BY-2 cell line (*Nicotiana tobacum* L. cv Bright yellow 2).

More particularly, after BY-2 cell was subcultured for three days, it was treated with the enzyme solution containing 2% cellulase R-10 and 0.5% macerozyme for 7 hours to isolate protoplasts.

The protoplast was diluted with MaMg buffer (0.4 M mannitol, 0.1% MES, 15 mM $MgCl_2$, pH 5.7) to have density of $2 \times 10^6$ cells/ml. 10 µg pSPran1-221 plasmid DNA and 10 µg pJD300 plasmid expressing luciferase(Luehrsen K R et al., 1992 Methods Enzymol., 16:3901-3907) were introduced into the protoplasts using the polyethylene glycol method and cultivated in the darkness at 23° C. for 16 hours. The cells were harvested from culture medium, then added lysis buffer (Luciferase assay, Promega) and sonicated to obtain the cell extract. The pJD300 plasmid is an internal control to calculate transformation efficiency. The 600 µl cell extract was mixed with 8 µl 25 mM MUG substrate and reacted at 37° C. for 1 hour. Then the reaction was stopped by O.2M $Na_2CO_3$ and the fluorescence of cell extract was measured at excitation 365 nm and emission 455 nm to investigate the activity of promotor. In addition luciferin of luciferase substrate was put into 1000 µl cell extract. Then the luminescence of the cell extract was measured immediately.

FIG. 6 show relative GUS/LUC activity that the GUS activity value of ibRan1 promoter is divided by luciferase activity value and calculated as percentage to 35S activity. As seen in FIG. 6, the result of transient assay shows that the activity of ibRan1 gene promoter is 25 times higher than that of CaMV 35S promoter. The value of FIG. 6 shows the means of triple replication.

Example 7

Identification of Oxidative Stress Induction of ibRan1 Promoter According to the Present Invention The GUS activity of transformant (F2) screened in example 5 was analysed quantitatively under the stress.

More particularly, the seeds of transgenic tobacco were germinated and 10 days old seedlings were transferred to MS medium containing 0.1M H₂O₂ and cultured for 24 hours. Then the seedlings were harvested and grinded in the GUS extract solution (50 mM sodium phosphate (pH 7.0), 10 mM EDTA, 0.1% Triton X-100, 0.1% sodium laurylsarcosine, and 10 mM β-mercaptoethanol). The mixed solution was centrifuged and the supernatant was harvested.

For cold treatment, 10 days old seedlings were cultured on MS medium at 4□ for 24 hours. Then the seedlings were grinded in the GUS extract solution and centrifuged to harvest the supernatant of the solution. The non-treatment samples were used as a control for comparison with the each stress treatment sample.

The harvested supernatant was mixed with 1 mM MUG (4-methylumbelliferyl glucuronide) and reacted at 37° C., followed by termination the reaction by adding 0.2M Na₂CO₃. The GUS activity of terminated reaction solution was measured at 365 nm and 455 nm using the fluorometer and the results were showed in the FIGS. 7 and 8.

The GUS activities in the FIGS. 7 and 8 were obtained analysis of three transformant lines (T2 plant) treated with oxidative or cold stress respectively. The result shows that by treating the H₂O₂, GUS activity of ibRan-7, ibRan-8, and ibRan-9 transformants containing sweetpotato ibRan1 gene promoter is increased 2.3 times, 3.5 times, and 3.8 times higher than that of control respectively. It is also showed that by treating the cold stress, GUS activity of ibRan-7, ibRan-8, and ibRan-9 transformants containing sweetpotato ibRan1 gene promoter is increased 2.1 times, 3.0 times, and 3.1 times higher than that of control respectively.

Example 8

Development of Transgenic Ginseng Using the pSPran1-101 Vector According to the Present Invention Stratified Korean ginseng (*Panax ginseng* C. A. Meyer) seeds were immersed in 70% ethanol for 1 min, then in 1% sodium hypochlorite solution for 1 hour, and washed three times with sterile distilled water. Zygotic embryos were removed from seeds and cultured on ½ MS (Murashige and Skoog 1962) medium with 1% sucrose and solidified with 0.27% gelrite. Cotyledon explants of zygotic embryos were used for culture materials.

The *A. tumefaciens* strain GV3101 was transformed with the pSPran1-101 vector constructed in Example 3. The *Agrobacterium* suspension was cultured for 24 hours at 25° C. in yeast extract broth (YEB) medium (5 g/L yeast extract; 5 g/L bacto-peptone, 5 g/L sucrose, pH with kanamycin 50 mg/L on a gyratory shaker (220 rpm). Cotyledon segments was dipped in the *Agrobacterium* solution for 5 min and blotted on sterile filter paper. These explants were co-cultured with *A. tumefaciens* in MS medium with 1.0 mg/L 2,4-D and 3% sucrose for 3 days, and then transferred to the same medium containing 400 mg/L cefotaxime for 2 weeks.

To select transformed somatic embryos, cotyledons containing somatic embryos were sub-cultured five times to the same medium containing 300 mg/L cefotaxime and 25 mg/L kanamycin by two weeks intervals. After kanamycin resistant somatic embryos were obtained, they were detached from explants and transferred to fresh medium with 50 mg/L kanamycin and 200 mg/L cefotaxime for plant conversion. All the embryogenic calluses were maintained at 24±2C under a 16-h (light)/8-h (dark) photoperiod for GUS activity assay. Nonembryogenic callus was selected through visual selection.

In order to induce adventitious roots, root segments of transgenic plants were cultured on a ½ MS medium that lacked NH₄NO₃ but contained 3.0 mg/L IBA and 3% (w/v) sucrose, which was solidified with 0.27% gelrite. After being adjusted to pH 5.8, the medium was autoclaved at 120° C. for 15 min. The petri dishes were incubated for 5 weeks under darkness at 22° C. and induced adventitious roots. To maintain the independent transgenic lines, adventitious roots were excised from the adventitious roots and subcultured onto the medium with the same composition as that for the initial root induction.

Example 9

Histochemical Staining Assay of Transgenic Cultured Callus and Root of Ginseng

The GUS activities of all screened ginseng transformants were analysed by histochemical staining assay. In the ginseng tissue culture, callus and adventitious root can be produced in a large quantities using the bioreactor. The activity of ibRan1 gene promoter in the callus and adventitious roots were analysed.

As shown in the FIG. 9, the strong GUS staining was observed in the transgenic callus containing pSPran1-101. The GUS activity of embryogenic callus showed stronger staining than that of nonembryogenic callus. Comparing the adventitious roots, the transgenic adventitious root with 35S were stained strongly at the tip of roots, whereas the transgenic adventitious root with pSPran1-101 were stained strongly all tissues including the tip of roots (FIG. 10).

INDUSTRIAL APPLICABILITY

As described hitherto, the present invention provides an high level expression promoter region derived from the sweetpotato (*Ipomoea batatas*) Ran GTPase gene (ibRan1) and 5'-untranslated region of the gene.

The promoter of Ran GTPase according to the present invention can induce high level expression of a foreign gene particularly in the tissues having active cell divisions for mass-accumlation of foreign protein in plant tissue cultured cells.

Therefore, the present invention is very useful in the generation of highly productive transgenic cultured cells to produce useful substances such as valuable medicinal and industrial proteins.

In addition, the promoter of Ran GTPase according to the present invention can be strongly induced in response to stresses, thus it can be applied for generation the transgenic plants resistant to the stresses.

The invention claimed is:

1. An isolated promoter of a Ran GTPase gene (ibRan1), said promoter comprising the nucleotide sequence of SEQ ID NO: 1.

2. An expression cassette comprising the isolated promoter of claim 1, wherein said expression cassette comprises a nucleic acid operably linked to said promoter, and wherein expression of said nucleic acid in a plant produces bioactive substances or proteins.

3. An expression cassette comprising the isolated promoter of claim 1, wherein said expression cassette comprises a nucleic acid operably linked to said promoter, and wherein expression of said nucleic acid in a plant confers resistance to stress.

4. An isolated 5'-untranslated region of a Ran GTPase gene (ibRan1) comprising the nucleotide sequence of SEQ ID NO: 2.

5. A binary vector for transforming plants, wherein the vector comprises
 a promoter of a Ran GTPase gene (ibRan1) comprising the nucleotide sequence of SEQ ID NO: 1; and
 a 5'-untranslated region of a Ran GTPase gene (ibRan1) comprising the nucleotide sequence of SEQ ID NO: 2.

6. A transient expression vector, wherein the vector comprises
 a promoter of a Ran GTPase gene (ibRan1) comprising the nucleotide sequence of SEQ ID NO: 1; and
 a 5'-untranslated region of a Ran GTPase gene (ibRan1) comprising the nucleotide sequence of SEQ ID NO: 2.

7. A transformant transformed with the isolated promoter of claim 1; wherein the transformant is a plant or bacteria.

8. A transformant transformed with the binary vector of claim 5; wherein the transformant is a plant or bacteria.

9. A transformant transformed with the transient expression vector of claim 6; wherein the transformant is a plant or bacteria.

10. A transgenic plant transformed with the isolated promoter of claim 1.

11. A transgenic plant transformed with the binary vector of claim 5.

12. A tissue cultured plant cell line transformed with the isolated promoter of claim 1.

13. A tissue cultured cell line transformed with the binary vector of claim 5; wherein the cell line is a plant or bacterial cell line.

14. A method for expressing a foreign sequence in plant cells or plant tissues, comprising
 introducing a vector comprising the isolated promoter of claim 1 operably linked to the foreign sequence into plant cells or plant tissues; and
 culturing the transformed plant cells or plant tissues under cultivation conditions.

15. A method for expressing a foreign sequence in plant cells or plant tissues, comprising
 introducing the binary vector of claim 5 into plant cells or plant tissues; and
 culturing the transformed plant cells or plant tissues under cultivation conditions; wherein the vector comprises the foreign sequence operably linked to the promoter.

* * * * *